United States Patent [19]

Sakai

[11] Patent Number: 5,203,342

[45] Date of Patent: Apr. 20, 1993

[54] PERIPHERAL BLOOD CIRCULATION STATE DETECTING APPARATUS

[75] Inventor: Hiroshi Sakai, Komaki, Japan

[73] Assignee: Colin Electronics Co., Ltd., Aichi, Japan

[21] Appl. No.: 701,058

[22] Filed: May 16, 1991

[30] Foreign Application Priority Data

Jun. 29, 1990 [JP] Japan .................................. 2-173975

[51] Int. Cl.[5] .............................................. A61B 5/02
[52] U.S. Cl. ..................................... 128/691; 128/633
[58] Field of Search ............... 128/633, 664, 665, 670, 128/691

[56] References Cited

U.S. PATENT DOCUMENTS 4,230,122 10/1980 Lübbers et al. ...................... 128/691
4,784,150 11/1988 Voorhies et al. .................... 128/664

OTHER PUBLICATIONS

Laid-open Publication No. 2-111344 of unexamined Japanese Patent Application (published in 1990) abstract only.
Laid-open Publication No. 64-56208 of unexamined Japanese Utility Model Application (published in 1989) abstract only.

Primary Examiner—Lee S. Cohen
Assistant Examiner—Kevin Pontius
Attorney, Agent, or Firm—Oliff & Berridge

[57] ABSTRACT

An apparatus for detecting a state of peripheral blood circulation of a subject, including a transmission type blood oxygen saturation measuring device emitting a plurality of lights having different wavelengths toward a subject, producing a photoelectric pulse wave signal indicative of intensity of each of the lights transmitted through the subject, and determining a first blood oxygen saturation by using the pulse wave signals corresponding to the transmitted lights; a reflection type blood oxygen saturation measuring device emitting a plurality of lights having different wavelengths toward the subject, producing a photoelectric pulse wave signal indicative of intensity of each of the lights reflected from the subject, and determining a second blood oxygen saturation by using the pulse wave signals corresponding to the reflected lights; and a determining device determining a state of peripheral blood circulation of the subject by utilizing a difference between the first and second blood oxygen saturations.

15 Claims, 3 Drawing Sheets

PERIPHERAL BLOOD CIRCULATION STATE DETECTING APPARATUS

BACKGROUND OF THE INVENTION

1. Field of the Invention

The present invention relates to an apparatus for detecting a state of peripheral blood circulation of a living body.

2. Related Art Statement

Peripheral blood circulation through peripheral blood vessels including capillaries spread in tissue of a patient is one of the most important indications that indicate physiological state of the patient. It is therefore required to accurately detect a state of the peripheral blood circulation. For monitoring the physiological state of circulatory organ of a patient who is undergoing a surgical operation, for example, it has conventionally been practiced to indirectly seize peripheral blood circulation state of the patient by measuring skin temperature of the patient.

However, patient's skin temperature may because of room temperature or other factors. It is therefore difficult to accurately detect a state of peripheral blood circulation of the patient by measuring the skin temperature. Thus, monitoring the physiological state of circulatory organ of the patient cannot be effected with sufficient reliability. With the conventional manner, the medical staff may fail to immediately find a shock of the patient during the surgical operation.

SUMMARY OF THE INVENTION

It is therefore an object of the present invention to provide an apparatus which detects a state of peripheral blood circulation of a subject with sufficient accuracy and which monitors the physiological state of circulatory organ of a subject with high reliability.

There is known a transmission-type oxymeter which non-invasively measures a blood oxygen saturation of a subject by utilizing the lights transmitted through the subject. In addition, there has recently been proposed a reflection-type oxymeter which utilizes the lights reflected from a subject for measuring a blood oxygen saturation of the subject. An example of the reflection-type oxymeter is disclosed in the Laid-Open Publication No. 2-111344 (Apr. 24, 1990) of unexamined Japanese Patent Application filed by the Assignee of the present application. Various studies and experiments carried out by the present inventor have elucidated that there is a characteristic difference between the blood oxygen saturations measured by the above-indicated two oxymeters, namely, transmission-type and reflection-type oxymeters. More specifically, the blood oxygen saturation measured by the transmission-type oxymeter does not vary in spite of changes of the peripheral blood circulation state of a patient who may be undergoing surgical operation, whereas the blood oxygen saturation measured by the reflection-type oxymeter varies with changes of the peripheral blood circulation state. The present invention has been developed based on this finding.

According to the present invention, there is provided an apparatus for detecting a state of peripheral blood circulation of a subject, comprising (a) transmission type blood oxygen saturation measuring means for emitting a plurality of lights having different wavelengths toward a subject, producing a photoelectric pulse wave signal indicative of intensity of each of the lights transmitted through the subject, and determining a first blood oxygen saturation by using the pulse wave signals corresponding to the transmitted lights, (b) reflection type blood oxygen saturation measuring means for emitting a plurality of lights having different wavelengths toward the subject, producing a photoelectric pulse wave signal indicative of intensity of each of the lights reflected from the subject, and determining a second blood oxygen saturation by using the pulse wave signals corresponding to the reflected lights, and (c) determining means for determining a state of peripheral blood circulation of the subject by utilizing a difference between the first and second blood oxygen saturations.

In the peripheral blood circulation state detecting apparatus constructed as described above, two blood oxygen saturations are measured by the transmission type and reflection type blood oxygen saturation measuring means, respectively. The blood oxygen saturation measured by the transmission type measuring means does not vary despite changes of peripheral blood circulation state of a subject, whereas the blood oxygen saturation measured by the reflection type measuring means varies with changes of the peripheral blood circulation state. Therefore, the peripheral blood circulation state of the subject can be determined by utilizing a difference between the two blood oxygen saturations measured by the different measuring means. The thus detected peripheral blood circulation state of the subject, who may be undergoing surgical operation, is more reliable than that detected by the conventional manner in which the peripheral blood circulation state is indirectly detected by measuring skin temperature of the patient. Thus, the present apparatus monitors the physiological state of circulatory organ of a patient with higher reliability, and immediately finds a patient in shock during surgical operation.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which.

DETAILED DESCRIPTION OF THE PREFERRED EMBODIMENT

Figure 1:
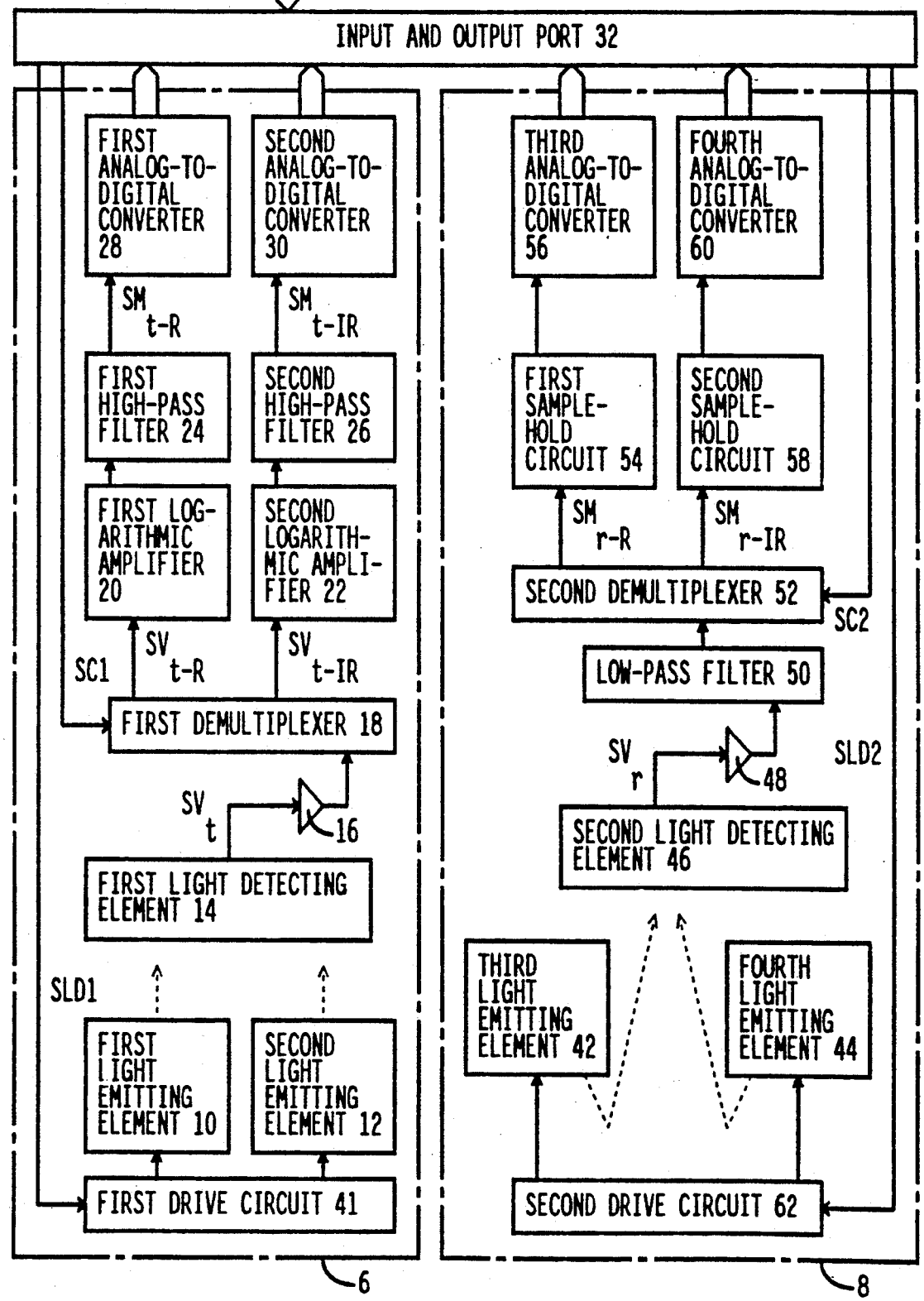
FIG. 1 is a diagrammatic view of a peripheral blood circulation state detecting apparatus embodying the present invention.

Referring first to FIG. 1, there is shown a peripheral blood circulation state detecting apparatus embodying the present invention. More specifically, FIG. 1 shows an electric circuit of the apparatus. The present apparatus detects a state of peripheral blood circulation of a subject. The term "peripheral blood" is used to mean the blood which flows through peripheral blood vessels including capillaries spread in tissue of a subject.

In FIG. 1, reference numeral 6 designates a transmission type blood oxygen saturation measuring circuit or first circuit for measuring a blood oxygen saturation of a subject by using different lights transmitted through the subject, and reference numeral 8 designates a reflection type blood oxygen saturation measuring circuit or second circuit for measuring a blood oxygen saturation of the subject by using different lights reflected from the subject. The first circuit 6 includes a first and a second light emitting element 10, 12 each of which is constituted by a light emitting diode (LED), for example. The first light emitting element 10 emits a red light having a wavelength of about 660 mµ, while the second light emitting element 12 emits an infrared light having a wavelength of about 804 mµ. However, a different pair of lights may be used. In fact, any pair of lights having different wavelengths may be employed so long as one of the two lights possesses significantly different absorption factors with respect to hemoglobin and oxygenated hemoglobin and the other light possesses essentially the same absorption factors with respect to the two hemoglobins.

The first and second light emitting elements 10, 12 alternately emit the red and infrared lights. A light emission from each light emitting element 10, 12 lasts for a predetermined duration of time. Each element 10, 12 emits the light at a predetermined frequency. The red and infrared lights emitted by the first and second light emitting elements 10, 12 are transmitted through a body portion of a subject, such as an auricle or finger (not shown), and the transmitted lights are detected by a common first light detecting element 14. The first light detecting element 14, which may be constituted by a photodiode, phototransistor, or photocell, generates an electric signal $SV_t$ whose magnitude corresponds to the detected amount or intensity of transmitted red and infrared lights. Signal $SV_t$ is supplied to a first demultiplexer 18 via a first amplifier 16. The first demultiplexer 18 is selectively placed in a first and a second position thereof by a switch signal SC1 (described below), in synchronism with the alternate light emissions from the first and second light emitting elements 10, 12. More specifically, when the first light emitting element 10 emits a red light, the first demultiplexer 18 is placed in the first position in which the demultiplexer 18 permits an electric signal $SV_{t-R}$ representative of the detected intensity of the transmitted red light, to be supplied to a first logarithmic amplifier 20. Meanwhile, when the second light emitting element 12 emits an infrared light, the first demultiplexer 18 is placed in the second position in which the demultiplexer 18 permits an electric signal $SV_{t-IR}$ representative of the detected intensity of the transmitted infrared light, to be supplied to a second logarithmic amplifier 22.

The first and second logarithmic amplifiers 20, 22 output logarithmic functions of electric signal $SV_{t-R}$, $SV_{t-IR}$ supplied from the first demultiplexer 18, and the logarithmic signals $SV_{t-R}$, $SV_{t-IR}$ are supplied to a first and a second high-pass filter 24, 26, respectively. The first and second high-pass filters 24, 26 supply pulse wave signals $SM_{t-R}$, $SM_{t-IR}$ to an input and output (I/O) port 32 via a first and a second analog to digital (A/D) converter 28, 30, respectively. More specifically, low frequency components are filtered off from the logarithmic signals $SV_{t-R}$, $SV_{t-IR}$ by the first and second high-pass filters 24, 26, so as to produce pulse wave signals $SM_{t-R}$, $SM_{t-IR}$ that are high frequency components corresponding to variations in intensity of the transmitted lights caused by arterial pulsation of the subject.

The I/O port 32 is connected via data bus to a central processing unit (CPU) 34, a read only memory (ROM) 36, a random access memory (RAM) 38, and a display device 40 such as a cathode ray tube (CRT). The CPU 34 operates for processing pulse wave signals $SM_{t-R}$, $SM_{t-IR}$ by utilizing control programs pre-stored in the ROM 36 and temporary-storage function of the RAM 38. More specifically, the CPU 34 generates a light emit signal SLD1 to a first drive circuit 41 via the I/O port 32 so that the first and second light emitting elements 10, 12 alternately and periodically emit red and infrared lights. In synchronism with the alternate and periodic red and infrared lights emissions from the first and second light emitting elements 10, 12, the CPU 32 generates switch signal SC1 to the first demultiplexer 18 so as to correspondingly place the demultiplexer 34 in the first or second position thereof. Accordingly, electric signals $SV_{t-R}$ and $SV_{t-IR}$ are distributed by the first demultiplexer 18 such that signal $SV_{t-R}$ representative of the transmitted red light is supplied to the first logarithmic amplifier 20 and, concurrently, signal $SV_{t-IR}$ representative of the transmitted infrared light is supplied to the second logarithmic amplifier 22. Further, the CPU 34 determines, by utilizing a pre-stored algorithm, an amplitude, $Amp_{t-R}$, $Amp_{t-IR}'$ of each of pulses with respect to each of pulse wave signals $SM_{t-R}$, $SM_{t-IR}$. The CPU 34 determines a blood or hemoglobin oxygen saturation, $OS_{a-t}$, corresponding to the transmitted lights, by utilizing a ratio of amplitude $Amp_{t-R}$ to amplitude $Amp_{t-IR}$ and a predetermined relationship between the blood oxygen saturation and the amplitude ratio, which relationship is pre-stored in the ROM 36. The CPU 34 commands the display device 40 to indicate the thus determined blood oxygen saturation $OS_{a-t}$.

Meanwhile, the second circuit 8 includes a group of third light emitting elements 42, a group of fourth light emitting elements 44, and a second light detecting element 46. The third and fourth light emitting elements 42, 44 are alternately and equiangularly provided on a circle whose center coincides with the position where the second light detecting element 46 is located. This arrangement is disclosed in the above-mentioned Laid-Open Publication No. 2-111344 of the Japanese Patent Application. The third and fourth light emitting elements 42, 44 emit the same red and infrared lights as those emitted by the first and second light emitting elements 10, 12. The red and infrared lights are emitted alternately and periodically by the first and second light emitting elements 10, 12. The red and infrared lights reflected by a body portion (not shown) of the subject are detected by the common second light detecting element 46.

The second light detecting element 46 generates an electric signal $SV_r$ whose magnitude corresponds to the detected amount or intensity of reflected red and infrared lights, to a low-pass filter 50 via a second amplifier 48. Noise having frequencies higher than those of pulse wave caused by arterial pulsation of the subject, is filtered out from electric signal SVr by the low-pass filter 50, so as to provide pulse wave signals, $SM_{r-R}$ and $SM_{r-IR}$, which respectively represent variations in intensity of reflected red or infrared light caused by the arterial pulsation. Signals $SM_{r-R}$, $SM_{r-IR}$ are supplied to a second demultiplexer 52. The second demultiplexer 52 selectively is placed in a first and a second position thereof by a switch signal SC2 (described blow), in synchronism with the alternate light emissions from the third and fourth light emitting elements 42, 44. More specifically, when the third light emitting elements 42 emit a red light, the second demultiplexer 52 is placed in the first position in which the demultiplexer 52 permits pulse wave signal $SM_{r-R}$ representative of the detected intensity of the reflected red light, to be supplied to the I/O port 32 via a first sample hold circuit 54 and a third A/D converter 56. When the fourth light emitting elements 44 emit an infrared light, the second demultiplexer 52 is placed in the second position in which the demultiplexer 52 permits pulse wave signal $SM_{r-IR}$ representative of the detected intensity of the reflected infrared light, to be supplied to the I/O port 32 via a second sample hold circuit 58 and a fourth A/D converter 60. The first and second sample hold circuits 54, 58 transmit pulse wave signals $SM_{r-R}$, $SM_{r-IR}$ supplied from the second demultiplexer 52, to the third and fourth A/D converters 56, 60, respectively, such that the circuits 54, 58 continue to hold the signals $SM_{r-R}$, $SM_{r-IR}$ received in a current cycle until the A/D converters 56, 60 complete the analog to digital conversion of the signals $SM_{r-R}$, $SM_{r-IR}$ which in the preceding cycle the converters 56, 60 had received from the circuits 54, 56, respectively.

The CPU 34 operates for processing pulse wave signals $SM_{r-R}$, $SM_{r-IR}$ by utilizing the temporary-storage function of the RAM 38 and the control programs pre-stored in the ROM 36. More specifically, the CPU 34 generates a light emit signal SLD2 to a second drive circuit 62 via the I/O port 32 so that the third and fourth light emitting elements 42, 44 alternately and periodically emit red and infrared lights, respectively. In synchronism with the alternate and periodic red and infrared lights emissions from the third and fourth light emitting elements 42, 44, the CPU 34 generates switch signal SC2 to the second demultiplexer 52 via the I/O port 32 so as to correspondingly place the demultiplexer 34 in the first or second position thereof. Thus, electric signal SVr is separated into pulse wave signals $SM_{r-R}$, $SM_{r-IR}$ by the second demultiplexer 52, and the separate signals $SM_{r-R}$, $SM_{r-IR}$ are distributed such that the signal $SM_{r-R}$ is supplied to the first sample hold circuit 54 and the signal $SM_{r-IR}$ is supplied to the second sample hold circuit 58. The CPU 34 processes the supplied pulse wave signals $SM_{r-R}$, $SM_{r-IR}$ by utilizing a suitable control program pre-stored in the ROM 36, and determines an amplitude, $Amp_{r-R}$, $Amp_{r-IR}$, of each of pulses with respect to each of pulse wave signals $SM_{r-R}$, $SM_{r-IR}$ by utilizing a pre-stored algorithm. In addition, The CPU 34 determines a blood oxygen saturation, $OS_{a-r}$, corresponding to the reflected lights, by using a ratio of amplitude $Amp_{r-R}$ to amplitude $Amp_{r-IR}$ and a predetermined relationship between the blood oxygen saturation and the amplitude ratio, which relationship is pre-stored in the ROM 36, and commands the display device 40 to indicate the thus determined blood oxygen saturation $OS_{a-r}$. Further, the CPU 34 determines a value indicative of a state of peripheral blood circulation of the subject by utilizing a difference between two blood oxygen saturations $OS_{a-t}$, $OS_{a-r}$. In the present embodiment, the CPU 34 determines a ratio of value $OS_{a-t}$ to value $OS_{a-r}$ as an index indicative of the peripheral blood circulation state. The CPU 34 commands the display device 40 to indicate the determined index $OS_{a-r}/OS_{a-t}$.

Figure 2:
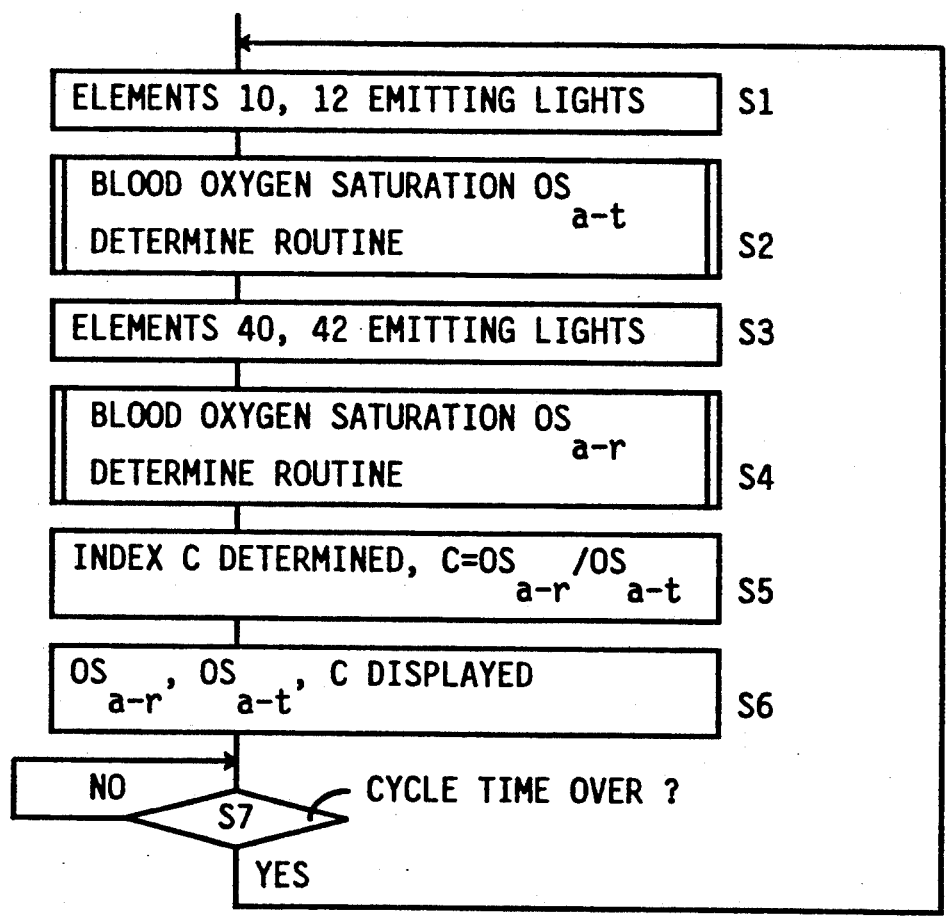
FIG. 2 is a flow chart for illustrating the operation of the apparatus of FIG. 2.

There will be described the operation of the present apparatus constructed as described above, for detecting the peripheral blood circulation state of a subject, by reference to the flow chart of FIG. 2.

First, in Step S1, the CPU 34 generates light emit signal SLD1 via the I/O port 32 to the first drive circuit 41 so that the first and the second light emitting elements 10, 12 alternately and periodically produce red and infrared light pulses, each pulse lasting for a predetermined time (e.g., 10 μsec), during a suitable period of time (e.g., one to two seconds). Step S1 is followed by Step S2, namely, the blood oxygen saturation $OS_{a-t}$ determine routine. In the routine of Step S2, a blood oxygen saturation $OS_{a-t}$ corresponding to the transmitted lights is determined by utilizing a ratio of amplitude $Amp_{t-R}$ of pulse wave signal $SM_{t-R}$ to amplitude $Amp_{t-IR}$ of pulse wave signal $SM_{t-IR}$ and a predetermined relationship between the blood oxygen saturation $OS_{a-t}$ and the amplitude ratio $Amp_{t-R}/Amp_{t-IR}$, according to the measuring principle disclosed in the Laid-Open Publication No. 64-56208 (Apr. 7, 1989) of unexamined Japanese Utility Model Application filed by the Assignee of the present application. In the present embodiment, the first circuit 6 and Steps S1, S2 correspond to transmission type blood oxygen saturation measuring means.

Step S2 is followed by Step S3 in which the CPU 34 generates light emit signal SLD2 via the I/O port 32 to the second drive circuit 62 so that the third and fourth light emitting elements 42, 44 alternately and periodically emit red and infrared light pulses, each pulse lasting for a predetermined time (e.g., 10 μsec), for a suitable period of time (e.g., one to two seconds). Step S3 is followed by Step S4, namely, the blood oxygen saturation $OS_{a-r}$ determine routine. In the routine of FIG. 4, a blood oxygen saturation $OS_{a-r}$ corresponding to the reflected lights is determined by utilizing a ratio of amplitude $Amp_{r-R}$ of pulse wave signal $SM_{r-R}$ to amplitude $Amp_{r-IR}$ of pulse wave signal $SM_{r-IR}$ and a predetermined relationship between the blood oxygen saturation $OS_{a-r}$ and the amplitude ratio $Amp_{r-R}/Amp_{r-IR}$, the same measuring manner as that disclosed in the above-mentioned Laid-Open Publication No. 2-111344 of the Japanese Patent Application. In the present embodiment, the second circuit 8 and Steps S3 and S4 correspond to reflection type blood oxygen saturation measuring means.

Figure 3:
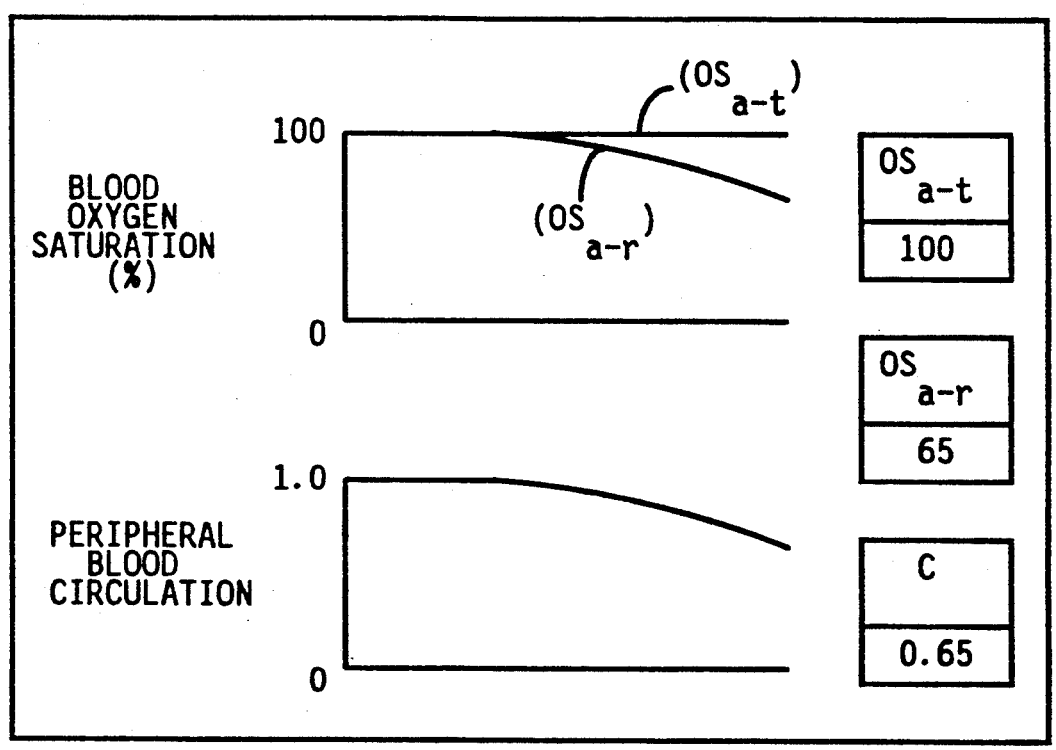
FIG. 3 is a view showing curves displayed on a display device 40 of the apparatus of FIG. 2, one of the curves representing a time-wise trend of the peripheral blood circulation state of a subject detected by the apparatus of FIG. 2.

Step S4 is followed by Step S5 in which the CPU 34 calculates a ratio, C $(=OS_{a-r}/OS_{a-t})$, of two blood oxygen saturations $OS_{a-r}$, $OS_{a-t}$, as an index indicative of a state of peripheral blood circulation of the subject. In the present embodiment, Step S5 corresponding to peripheral blood circulation state determining means. Smaller values C indicate worse states of peripheral blood circulation. Step S5 is followed by Step S6 in which the CPU 34 commands the display device 40 to indicate the two blood oxygen saturations $OS_{a-t}$, $OS_{a-r}$ and index C on a CRT screen thereof, as shown in FIG. 3. FIG. 3 shows three curves representing time-wise trends of respective measurements $OS_{a-t}$, $OS_{a-r}$ and C. The display 40 also provides digital presentations of the last determined values $OS_{a-t}$, $OS_{a-r}$, C. The two curves shown in the upper graph of FIG. 3 indicates that both the blood oxygen saturations $OS_{a-t}$ and $OS_{a-r}$ are at 100% at the left-hand ends of the curves which ends correspond to a point of commencement of a surgical operation conducted on a patient. This is why the patient is in an unusual situation under general anesthesia and artificial respiration. Generally, an initial value of blood oxygen saturation $OS_{a-r}$ does not coincide with that of blood oxygen saturation $OS_{a-t}$. Step S6 is followed by Step S7 in which the CPU 34 decides whether or not a predetermined cycle time has passed after the start or end of the measurements $OS_{a-t}$, $OS_{a-r}$, C at the current cycle. If a negative decision is made in Step S7, the CPU 34 waits for an affirmative decision being made in Step S7. On the other hand, when an affirmative decision is made, the control of the CPU 34 goes back to Step S1 and the following steps. In this way, two blood oxygen saturations $OS_{a-t}$, $OS_{a-r}$ and index C are periodically determined, and indicated on the display 40, at respective measuring cycles.

As is apparent from the foregoing description, the present apparatus determines two blood oxygen saturations $OS_{a-t}$, $OS_{a-r}$ corresponding to the transmitted lights and the reflected lights. Since the first blood oxygen saturation $OS_{a-t}$ corresponding to the transmitted lights does not vary in spite of changes of the peripheral blood circulation state but the second blood oxygen saturation $OS_{a-r}$ corresponding to the reflected lights varies because of changes of the peripheral blood circulation state, the changes of the peripheral blood circulation state are detected by utilizing a difference between the two blood oxygen saturations $OS_{a-r}$, $OS_{a-t}$. Therefore, index C, namely, ratio of second blood oxygen saturation $OS_{a-r}$ to first blood oxygen saturation $OS_{a-t}$, represents the peripheral blood circulation state of the subject, with high reliability. Periodic measurements and presentations of blood oxygen saturations $OS_{a-r}$, $OS_{a-t}$ and index C during a surgical operation of a patient assure the medical staff of more reliable seizure of the peripheral blood circulation state of the patient than the conventional manner in which the peripheral blood circulation state is indirectly seized by measuring skin temperature of the patient. The present apparatus also immediately finds a patient in shock during surgical operation.

While, in the present embodiment, peripheral blood circulation state is detected by determining a ratio of second blood oxygen saturation $OS_{a-r}$ to first blood oxygen saturation $OS_{a-t}$, the circulation state may be detected by actually determining a difference between the two saturations $OS_{a-r}$, $OS_{a-t}$. In this case, the determined difference value per se may be used as an index indicative of the circulation state, or alternatively, a value corresponding to the determined difference may be used as such an index. According to the principle of the present invention, it is possible to adapt the illustrated embodiment in any way in which peripheral blood circulation state of a subject is detected by utilizing the fact that difference is observed between two blood oxygen saturations measured by the transmission type and reflection type measuring means.

Although, in the illustrated embodiment, index C is presented on the CRT display 40 both in the form of a curve and in the form of digits, as seen in FIG. 3, it is possible to present index C in only one of the two forms. Furthermore, in addition to, or in place of the presentation of index C, the embodiment may be adapted to indicate a warning message on the display 40, or produce an alarm sound from a speaker, in the event that index C is decreased to below a predetermined lower limit.

While, in the illustrated embodiment, the apparatus is used for monitoring peripheral blood circulation state of a subject and thereby monitoring physiological state of the circulatory organ of the subject, who may be undergoing a surgical operation, the apparatus may be used for other applications, for example, identifying the cause of muscle pain such as stiffened shoulder. More specifically, in the event that the present apparatus provides a low index value C with respect to tissue near the skin around a body portion having muscle pain, it is speculated that the muscle pain is because of a bad state of peripheral blood circulation. On the other hand, in the event that index C shows a good value, it is estimated that the cause of the muscle pain would be, for example, due to nerves. In this case, the reflection type blood oxygen saturation measuring means is used for measuring a blood oxygen saturation from the tissue around the body portion in question.

While the present invention has been described in its presently preferred embodiment, it is to be understood that the invention is by no means limited to the details of the illustrated embodiment but may be embodied with various changes, modifications and improvements that may occur to those skilled in the art without departing from the spirit and scope of the invention defined in the appended claims.

What is claimed is:

1. An apparatus for detecting a state of peripheral blood circulation of a subject, comprising:
    transmission type blood oxygen saturation measuring means for emitting a plurality of lights, each light having a different wavelength, toward said subject, producing a photoelectric pulse wave signal indicative of intensity of each of the lights transmitted through said subject, and determining a first blood oxygen saturation by using the pulse wave signals corresponding to the transmitted lights;
    reflection type blood oxygen saturation measuring means for emitting a plurality of lights, each light having a different wavelength toward said subject, producing a photoelectric pulse wave signal indicative of intensity of each of the lights reflected from said subject, and determining a second blood oxygen saturation by using the pulse wave signals corresponding tot he reflected lights; and
    peripheral blood circulation determining means for determining a state of peripheral blood circulation of said subject by utilizing a difference between said first and second blood oxygen saturations.

2. An apparatus according to claim 1, wherein said transmission type blood oxygen saturation measuring means comprises:
    a pair of light emitting elements emitting a red and an infrared light, respectively;
    a light detecting element detecting the red and infrared lights transmitted through a body portion of said subject, and generating the photoelectric pulse wave signals corresponding to the transmitted red and infrared lights; and
    first blood oxygen saturation determining means for determining said first blood oxygen saturation by utilizing amplitudes of said photoelectric pulse wave signals.

3. An apparatus according to claim 1, wherein said reflection type blood oxygen saturation measuring means comprises:
    a pair of light emitting elements emitting a red and an infrared light, respectively;
    a light detecting element detecting the red and infrared lights reflected from a body portion of said subject, and generating the photoelectric pulse wave signals corresponding to the reflected red and infrared lights; and
    second blood oxygen saturation determining means for determining said second blood oxygen saturation by utilizing amplitudes of said photoelectric pulse wave signals.

4. An apparatus according to claim 1, wherein said peripheral blood circulation determining means calculates a ratio of said second blood oxygen saturation to said first blood oxygen saturation, said ratio representing said state of peripheral blood circulation of said subject.

5. An apparatus according to claim 1, wherein said peripheral blood circulation determining means calculates a difference value between said first and second blood oxygen saturations, said difference value representing said state of peripheral blood circulation of said subject.

6. An apparatus according to claim 1, wherein said peripheral blood circulation determining means periodically determines a value indicative of said state of peripheral blood circulation of said subject, at regular intervals of time.

7. An apparatus according to claim 6, further comprising display means for indicating a curve representative of a time-wise variation of the values periodically determined by said peripheral blood circulation determining means.

8. An apparatus according to claim 7, wherein said display means also provides a digital presentation of the value determined by said determining means at a last one of the periodically determined values.

9. An apparatus according to claim 6, further comprising warning means for informing an operator that said value determined by said peripheral blood circulation determining means is reduced to below a predetermined reference value.

10. A peripheral blood circulation monitor for monitoring peripheral blood circulation of a subject, comprising:

transmission type blood oxygen saturation measuring means for emitting a first light having a first wavelength and a second light having a second wavelength different from said first wavelength, each toward a body portion of said subject, producing a first photoelectric pulse wave signal indicative of an intensity of the first light transmitted through said body portion of said subject and a second photoelectric pulse wave signal indicative of an intensity of the second light transmitted through said body portion of said subject, and determining a first blood oxygen saturation based on said first and second pulse wave signals;

reflection type blood oxygen saturation measuring means for emitting a third light having a third wavelength and a fourth light having a fourth wavelength different from aid third wavelength, each toward said body portion of said subject, producing a third photoelectric pulse wave signal indicative of an intensity of the third light reflected from said body portion of said subject and a fourth photoelectric pulse wave signal indicative of an intensity of the fourth light reflected from said body portion of said subject, and determining a second blood oxygen saturation based on said third and fourth pulse wave signals;

peripheral blood circulation determining means for periodically determining a value representative of a state of peripheral blood circulation of said subject, based on a difference between said first and second blood oxygen saturations, at regular intervals of time; and informing means for comparing each of the values determined by said peripheral blood circulation determining means, with a predetermined reference value, and informing an operator of the comparison result.

11. The peripheral blood circulation monitor according to claim 10, wherein said informing means comprises display means for displaying, based on said comparison result, a warning message that said value is smaller than said reference value.

12. The peripheral blood circulation monitor according to claim 10, wherein said peripheral blood circulation determining means periodically determines a ratio of said second blood oxygen saturation to said first blood oxygen saturation, said ratio representing said state of peripheral blood circulation of said subject.

13. The peripheral blood circulation monitor according to claim 10, wherein said peripheral blood circulation determining means periodically determines a difference value between said firs and second blood oxygen saturations, said difference value representing said state of peripheral blood circulation of said subject.

14. The peripheral blood circulation monitor according to claim 10, further comprising display means for indicating a curve representative of a time-wise variation of the values periodically determined by said peripheral blood circulation determining means.

15. The peripheral blood circulation monitor according to claim 14, wherein said display means provides a digital presentation of the value determined by said peripheral blood circulation determining means in a last one of said regular intervals of time.

* * * * *